US009387270B2

(12) United States Patent
Piper

(10) Patent No.: US 9,387,270 B2
(45) Date of Patent: Jul. 12, 2016

(54) METHOD AND APPARATUS TO DISPENSE FRAGRANCE INTO THE AIR IN A BOWLING STRUCTURE

(71) Applicant: Elizabeth K Piper, Avondale, AZ (US)

(72) Inventor: Elizabeth K Piper, Avondale, AZ (US)

(*) Notice: Subject to any disclaimer, the term of this patent is extended or adjusted under 35 U.S.C. 154(b) by 0 days.

(21) Appl. No.: 13/694,770

(22) Filed: Jan. 3, 2013

(65) Prior Publication Data

US 2016/0095950 A1    Apr. 7, 2016

Related U.S. Application Data

(60) Provisional application No. 61/668,856, filed on Jul. 6, 2012, provisional application No. 61/631,371, filed on Jan. 3, 2012.

(51) Int. Cl.
*B05D 1/28* (2006.01)
*A61L 9/04* (2006.01)
*A63D 5/10* (2006.01)

(52) U.S. Cl.
CPC .... *A61L 9/04* (2013.01); *A63D 5/10* (2013.01)

(58) Field of Classification Search
CPC ....................................................... A63D 5/10
See application file for complete search history.

(56) References Cited

U.S. PATENT DOCUMENTS

| 4,036,496 | A  | * | 7/1977  | Robinson ............... A63D 1/04 106/287.14 |
| 4,487,788 | A  | * | 12/1984 | Scheie ..................... G01N 1/04 427/9 |
| 5,641,538 | A  | * | 6/1997  | Caffrey .................. A47L 11/03 427/428.03 |
| 5,650,012 | A  | * | 7/1997  | Davis ..................... A47L 11/03 118/207 |
| 7,784,147 | B2 | * | 8/2010  | Burkholder ............ A47L 11/03 118/207 |
| 2002/0147053 | A1 | * | 10/2002 | Chrisman, III .... A63B 37/0001 473/125 |
| 2007/0167348 | A1 | * | 7/2007  | Hirsch .................... A61K 36/63 512/1 |
| 2007/0289086 | A1 | * | 12/2007 | Davis ..................... A63D 5/10 15/340.3 |

* cited by examiner

*Primary Examiner* — Nathan Empie
(74) *Attorney, Agent, or Firm* — Tod R. Nissle, P.C.

(57) ABSTRACT

A method to condition the air in a bowling alley utilizes an oil mixture which is dispensed by conditioning apparatus which down and up a synthetic bowling lane. The oil mixture comprises original lane oil and a fragrance composition which admixed to the oil mixture to produce a fragrant lane oil which has at 1700 $cm^{-1}$ a % T which is generally equivalent to the % T of the original lane oil.

1 Claim, 5 Drawing Sheets

METHOD AND APPARATUS TO DISPENSE FRAGRANCE INTO THE AIR IN A BOWLING STRUCTURE

This application claims priority based on U.S. Provisional Patent Application Ser. No. 61/668,856 filed Jul. 6, 2012. This application also claims priority based on U.S. Provisional Patent Application Ser. No. 61/631,371 filed Jan. 3, 2012.

This invention pertains to conditioning air.

More particularly, the invention relates to an apparatus and method to condition the air in a bowling alley.

A variety of methods and apparatus are available for conditioning air. One method for conditioning air comprises dispensing a fragrance into the air by means of an aerosol or by means of a free standing dispense which contains a high concentration of fragrance which is carried into the air by way of evaporation or other delivery mechanisms. Those of skill in the art have long endeavored to provide improved air conditioning methods and apparatus. Accordingly, it would be highly desirable to provide an improved method and apparatus to condition air.

Therefore, a principal object of the instant invention is to provide an improved method and apparatus to condition air.

This, and further and other objects of the invention will be apparent to those skilled in the art from the following description taken in conjunction with the drawings in which.

Figure 1:
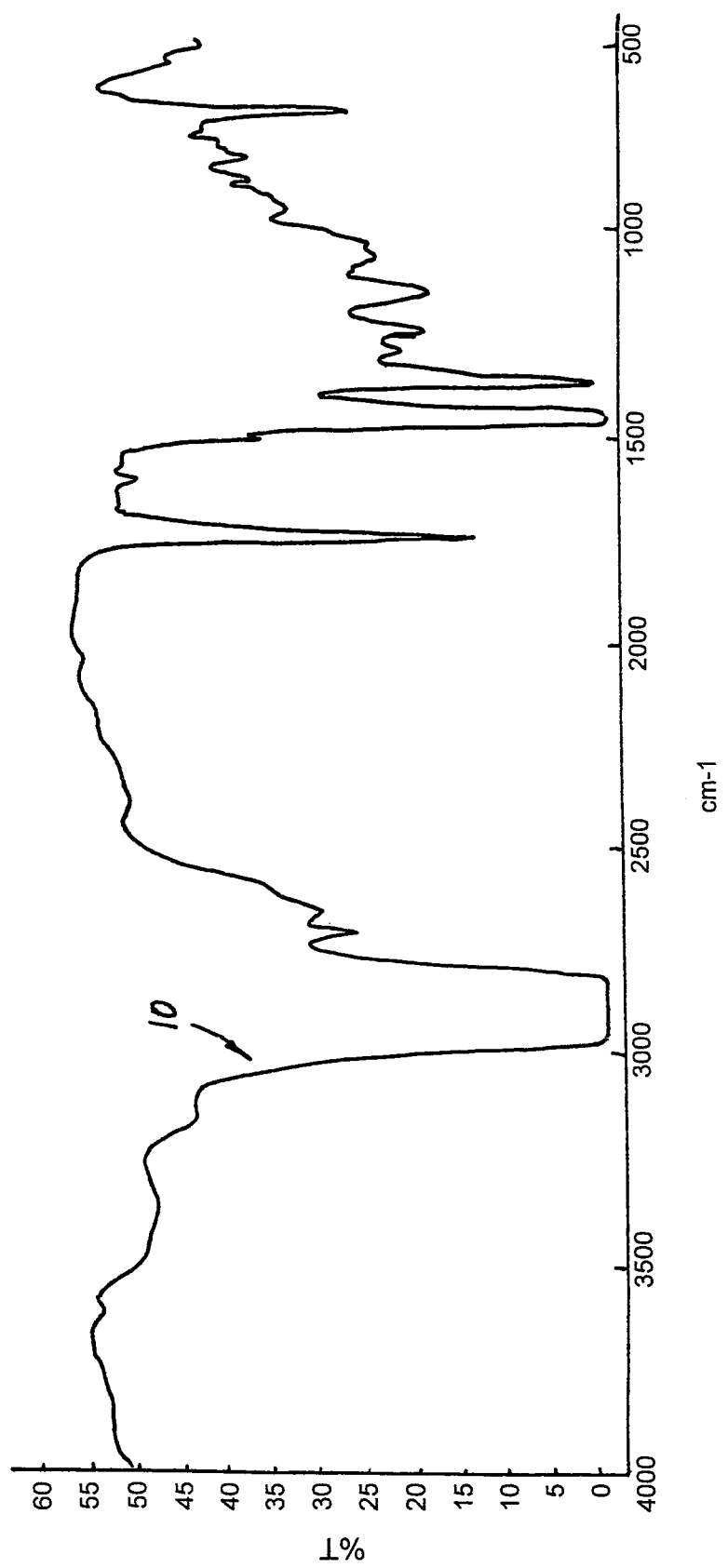
FIG. 1 is a graph illustrating an FTIR (Fourier Transform Infrared Spectrophotometry) scan of a fragrance composition utilized in the practice of the invention.

Briefly, in accordance with the invention, I provide an improved method to condition the air in a bowling alley. The method comprises the steps of providing an enclosed building structure; and providing a plurality of synthetic bowling lanes in the structure. Each of the lanes includes a first end with a base line, includes a second end located under a pin setter, and extends from the first end to the second end. The method also includes the step of providing a conditioning apparatus to apply lane oil separately to only a selected portion of each of the bowling lanes. The conditioning apparatus includes a reservoir to store a selected quantity of lane conditioning oil for dispensation on bowling lanes, and an oil dispensation mechanism to dispense oil at varying rates at different locations along a bowling lane while moving both toward the pin setter, and away from the pin setter. The method also includes the step of shipping from a remote location to the building structure one or more containers of lane conditioning oil. The lane conditioning oil comprises over 50% by weight mineral oil and has a medium to high viscosity in the range of 28.0 to 40.0 cSt at 40 degrees C. and has a surface tension in the range of 25 to 30 dynes/cm. The method also includes the step of shipping from a remote location to the building structure at least one container of a first fragrance composition. The first fragrance composition comprises a fragrance oil and carrier and is miscible in the lane conditioning oil in a proportion of fragrance composition to lane oil in the range of 1:80 to 1:10. The method also includes the step of shipping from a remote location to the building structure at least one container of a second fragrance composition. The second fragrance composition comprises a fragrance oil and carrier and is miscible in the lane conditioning oil in a proportion of fragrance composition to lane oil in the range of 1:80 to 1:10. The second fragrance composition has a scent different from the scent of the first fragrance composition. The method also includes the step of homogeneously admixing the first fragrance composition and the lane conditioning oil in a proportion in the range of 1:80 to 1:10 to produce a first fragrant lane oil to produce a first fragrant lane oil having in an FTIR a % T at 1700 cm$^{-1}$ that is within 5% or less of the % T of said lane oil at 1700 cm$^{-1}$; and, of utilizing the conditioning apparatus to apply the first fragrant lane oil to one of the synthetic lanes. The conditioning apparatus applies the first fragrant lane oil while the conditioning apparatus is both moving away from and moving toward the base line such that the maximum thickness of the first fragrant lane oil on the lane adjacent the base line is at least thirty units; such that the maximum thickness of the first fragrant lane oil a first selected distance away from the base line is less than fifteen units; and, such that there is no first fragrant lane oil a second selected distance away from the base line, the second selected distance being greater than the first selected distance. The improved method also includes the step of, after a selected period of time has passed from applying the first fragrant lane oil, of homogeneously admixing the second fragrance composition and the lane oil in a proportion in the range of 1:80 to 1:10 to produce a second fragrant lane oil to produce a first fragrant lane oil having in an FTIR a % T at 1700 cm$^{-1}$ that is within 5% or less of the % T of said lane oil at 1700 cm$^{-1}$; and, of utilizing the conditioning apparatus to apply the second fragrant lane oil to one of the synthetic lanes. The conditioning apparatus applies the second fragrant lane oil while the conditioning apparatus is both moving away from and moving toward the base line such that the maximum thickness of the second fragrant lane oil on the lane adjacent the base line is at least thirty units; such that the maximum thickness of the second fragrant lane oil a first selected distance away from the base line is less than fifteen units; and, such that there is no second fragrant lane oil a second selected distance away from the base line, the second selected distance being greater than the first selected distance.

In accordance with a preferred embodiment of the invention, an enclosed building structure is provided. Bowling ordinarily is accomplished in a enclosed building so that the environment around bowling lanes can be controlled and so that the pin setters, bowling lanes, and other equipment in the bowling alley can be protected from the elements. The method of the invention is preferably carried out on synthetic bowling lanes and not on lanes made from wood. While the material utilized to produce a synthetic bowling lane can vary, one kind of synthetic material utilized to produce a synthetic bowling lane comprises a compressed, resin impregnated, pressurized high temperature laminate. As seen below, in the practice of the invention, one or more fragrance composition(s) is admixed with lane oil. One of the primary requirements of a fragrance composition is that it be miscible with lane oil. It is desirable to be able to focus on this requirement without concern whether a particular fragrance composition will be injurious to wood in the event wood is utilized to construct a bowling lane. Accordingly, the invention preferably is utilized in conjunction with bowling lanes constructed from synthetic material.

Each synthetic bowling lane includes a first end with a base line; includes a second end located under a pin setter; and, extends from the first end to the second end. A base line marks the beginning of the first end of the bowling lane. When a bowler is releasing a bowling ball, the bowler's feet can not, while the bowler is moving toward the blowing lane, cross the base line and move "down lane" toward the pin setter. Each lane has a width which typically is forty to forty-two boards wide.

Kegel™ conditioning apparatus or other conditioning equipment is provided in order to apply lane conditioning oil to a bowling lane. The conditioning apparatus applies a coating of lane oil to only selected portions of a bowling lane. The approximate distance from the base line of a bowling lane to the pin setter at the second end of the bowling lane is about sixty feet. Oil typically is only applied to the first thirty-nine to forty-five feet of the lane which extends "down lane" toward the pin setter, and is not applied to the remaining portion of the lane. The point "down lane" at which the oil coating ends is called the "buff line". Consequently, the buff line is spaced apart from the base line and from the points at which pins are set by the pin setter on the second end of the bowling lane.

The conditioning apparatus includes a reservoir to store a selected quantity of lane conditioning oil for dispensation on bowling lanes, and includes an oil dispensation mechanism to dispense oil at varying rates at different locations along a bowling lane while moving both toward the pin setter and away from said pin setter.

The composition of lane conditioning oil can vary as desired; however, lane conditioning oils often comprise over 50%, preferably over 85%, by weight mineral oil. The lane conditioning oil is transported in containers to the building structure from a location remote from the building structure. A single container at a time can be transported to the building structure, but two or more containers typically are transported at one time.

One function of lane oil is to protect the surface of the lane. Another function is to help guide a bowling ball. The viscosity of lane oil can vary as desired; for example, from about 12 to 85 centipoise. When the temperature in a bowling alley is, however, in the range of 68 to 80 degrees F., it is generally preferable in the practice of the invention to utilize lane oils having a medium to high viscosity in the range of 28.0 to 40.0 cSt at 40 degrees C. and having a surface tension in the range of 25 to 30 dynes/cm. Examples of such lane conditioning oils are, without limitation, the Navigate™, Infinity™, Prodigy™, Defense-S™, and Offense HV™ products made by Kegel. Importantly, a medium to high viscosity reduces the likelihood that a fragrance composition added in small quantities to the lane oil will adversely affect the viscosity or desired functioning of the lane oil. This has, to date, generally proven to true in the practice of the invention. An unexpected added benefit encountered in the practice of the invention is that utilization of fragrance compositions has not downgraded the performance of a conditioning machine utilized over an extended period of time to apply lane oil.

The fragrance compositions provided in the practice of the invention comprise a fragrance oil and carrier, and the fragrance compositions are miscible in lane conditioning oils in a proportion of fragrance composition to lane conditioning oil in the range of 1:80 to 1:10. The fragrance compositions comprise a fragrance oil and a carrier. The fragrance oil typically is a blended synthetic aroma compound or is a natural essence oil. The natural essence oil is a highly fragrant essence extracted from a plant by distillation, fast evaporation, or other appropriate techniques. The carrier can, by way of example and not limitation, comprise propylene glycol, vegetable oil, or mineral oil. Since mineral oil typically comprises a high proportion of lane oil, a fragrance composition comprising fragrance oil and mineral oil is preferred in one embodiment of the invention. The proportions of a fragrance oil(s) and if a carrier(s) in a fragrance composition can vary as desired. Providing a plurality of different fragrance compositions each having a different scent is desired in the practice of the invention and is believed important in attracting bowlers to a particular bowling alley. Utilizing the same scent continuously still benefits the environment in a bowling alley; yet, periodically altering on a weekly, monthly, or some other predetermined basis the scent utilized, is normally more appealing to bowlers. When the time periods during which a particular scent is utilized vary, the unexpected introduction of a new scent is a factor which often makes attending a bowling alley more interested to bowlers.

The fragrance compositions are shipped in containers to the building structure from a location remote from the building structure. The fragrance compositions can be shipped one container at a time or two or more containers can be shipped at the same time to the building structure. Although the size of the fragrance containers can vary as desired, each fragrance container presently holds a relatively small amount of a fragrance composition, for example, one ounce. This contrasts with the quantity of lane oil found in each container of lane oil. Each container of lane oil typically is significantly larger than a container of fragrance and may hold forty ounces or more of lane oil. Since the size of each fragrance container may be relatively small, and since it is important in one preferred embodiment of the invention to provide different fragrance compositions each having a different scent, it is more likely that two or more fragrance containers will be shipped at the same time from a remote location to the building structure.

The fragrance compositions presently, but not necessarily, are utilized in combination with lane conditioning oil in fairly small proportions typically such that the proportion of fragrance composition to lane conditioning oil is in the range of 1:80 to 1:10. A fragrance composition can be admixed with lane oil at any time prior to adding the lane oil to the oil reservoir in the conditioning apparatus, but in one presently preferred embodiment of the invention, when lane conditioning oil is added to the oil reservoir in the conditioning apparatus, the fragrance composition also added. Currently, one-half ounce to two ounces of fragrance composition is added to each forty ounces of lane oil. When the lane oil and miscible fragrance composition are added to the oil reservoir, they admix and combine and produce a generally homogeneous fragrant lane oil.

When the conditioning apparatus is utilized to apply a fragrant lane oil, the fragrant lane oil is applied both while the conditioning apparatus is moving away from the base line and then moving back toward the base line. Applying the fragrant lane oil both while the conditioning apparatus or moving away from and back toward the base line, increases the fresh surface area which is exposed to air when the first fragrant lane oil is being applied and facilitates dispensation into the air of the scent in the fragrant lane oil.

A fragrant lane oil typically, but not necessarily, is applied to a synthetic lane such that the maximum thickness of the fragrant lane oil coating on the lane adjacent the base line is at least thirty units, such that the maximum thickness of the fragrant lane oil coating a first selected distance away from the base line is less than fifteen units, and such that there is no fragrant lane oil a second selected distance (i.e., at the buff line and beyond) away from the base line, where the second selected distance is greater than the first selected distance. Just prior to the buff line, the thickness of the fragrant lane oil coating may, for example, be about three units. The maximum thickness of lane oil near the base line can be in the range of twenty to 100 units, if desired, but is, as noted, typically at least thirty units.

In one embodiment of the invention, after a selected period of time passes after application to a first bowling lane of a first fragrant lane oil having a first scent, a second fragrant lane oil is produced by adding a second fragrance composition to lane conditioning oil which has not yet been treated with a fragrance composition. The second fragrance composition has and produces in the lane conditioning oil a second scent which is different from the first scent scent. The second fragrant lane oil is applied to the first bowling lane by the conditioning apparatus. Ordinarily, the first fragrant lane oil is removed from the first bowling lane before the second fragrant lane oil is applied; or, the second fragrant lane oil is applied to a bowling lane other than the first bowling lane.

If desired, first and second fragrance compositions each having a different scent can be admixed to produce a third fragrance composition having a scent different from the scent of either the first and second fragrance compositions. The third fragrance composition can the be admixed with lane conditioning oil. Or the first and second fragrance compositions can be admixed simultaneously with lane conditioning oil.

Equipment to measure units of thickness of a coating of oil on a bowling lane is well known in the art and is not described herein.

When oil is applied to a particular portion of a bowling lane, the thickness of the oil tends to be greatest, or at a maximum, near the center of the lane and to less near the peripheral edges of the lane. The peripheral edges or sides of a lane are spaced apart and parallel to one another and extend from the base line down to the pin setter and second end of the bowling lane.

One way to evaluate the compositions of lane oil and of fragrance compositions is to utilize a FTIR (Fourier Transform Infrared Spectrophotometry) scan.

FIG. 1 is an illustration of the FTIR scan of a lane oil utilized in the practice of the invention. In FIGS. 1 to 5, the vertical leg of the graph, labeled % T, indicates percent transmittance, while the horizontal leg of the graph, labeled $cm^{-1}$, is used to indicate absorbance per centimeter. The data points obtained during the FTIR scan produce graph line 10.

Figure 2:
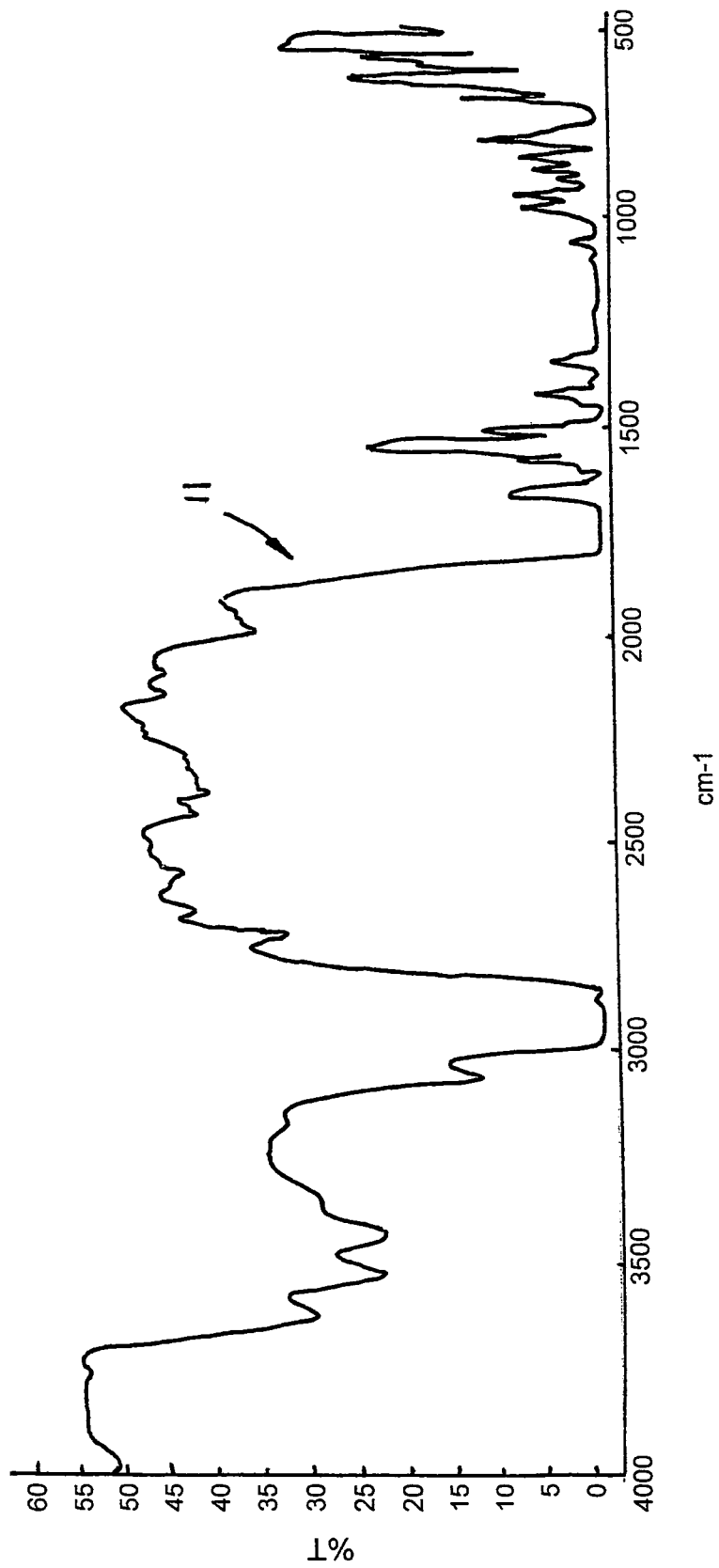
FIG. 2 is a graph illustrating an FTIR scan of a lane oil used to intermittently coat synthetic bowling lanes in a bowling alley.

FIG. 2 is an illustration of the FTIR scan of a fragrance composition utilized in the practice of the invention. The data points obtained during the FTIR scan produce graph line 11.

Figure 3:
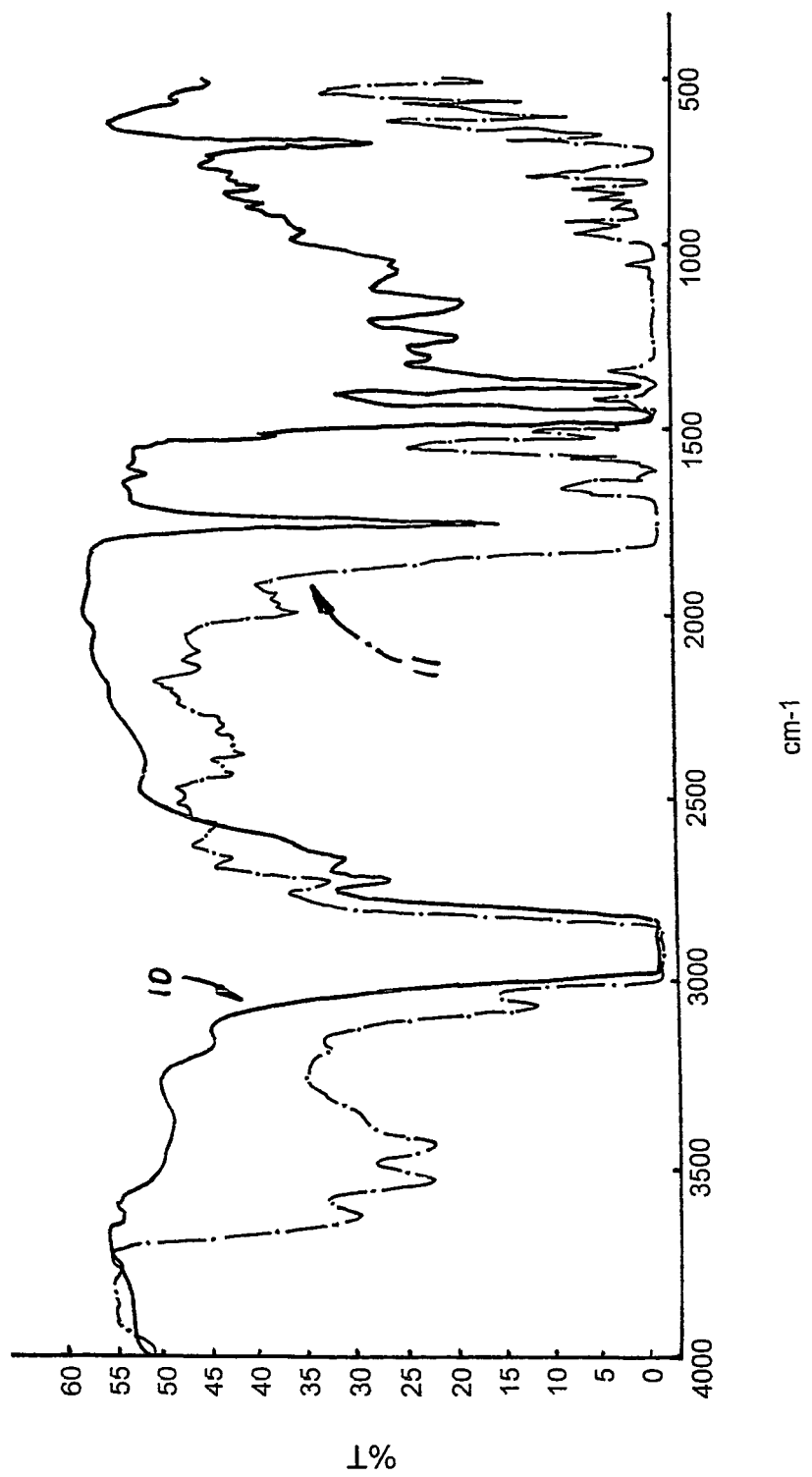
FIG. 3 is a graph illustrating an overlay of the FTIR scans of FIGS. 1 and 2.

FIG. 3 is an overlay combining and illustrating together graph lines 10 and 11 from FIGS. 1 and 2. In FIG. 3, graph line 11 is in dot-dash form, while graph line 10 is in continuous solid form.

As can be seen in FIG. 3, the FTIR scans of one lane oil and one fragrance composition have similarities.

Figure 4:
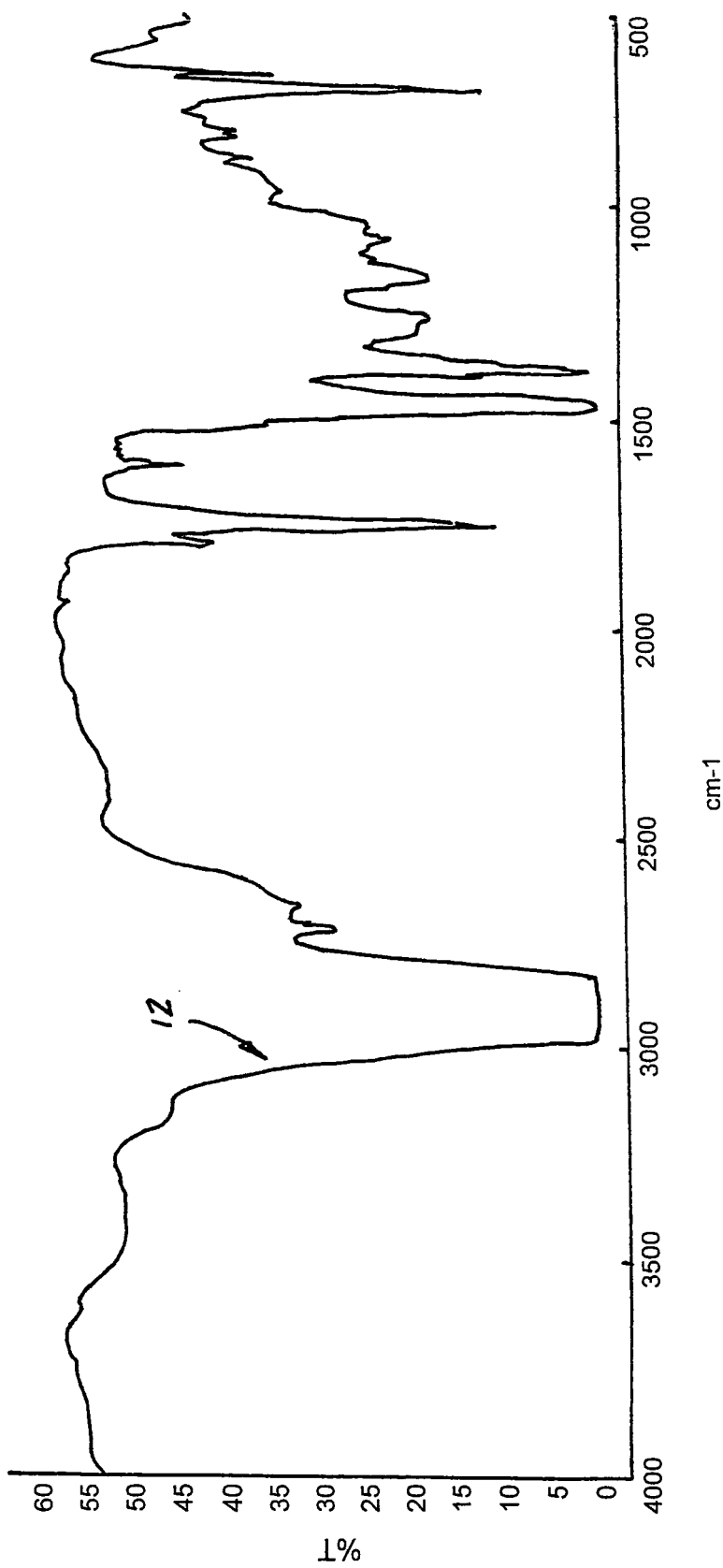
FIG. 4 is a graph illustrating an FTIR scan of the lane oil of FIG. 2 combined with the fragrance composition of FIG. 1; and, FIG. 5 is a graph illustrating an overlay of the FTIR scans of FIGS. 2 and 4.

FIG. 4 is an illustration of the FTIR scan of the lane oil of FIG. 1 after the miscible fragrance composition of FIG. 2 has been added to the lane oil to produce a homogeneous fragrant lane oil composition. The data points obtained during the FTIR scan produce graph line 12.

Figure 5:
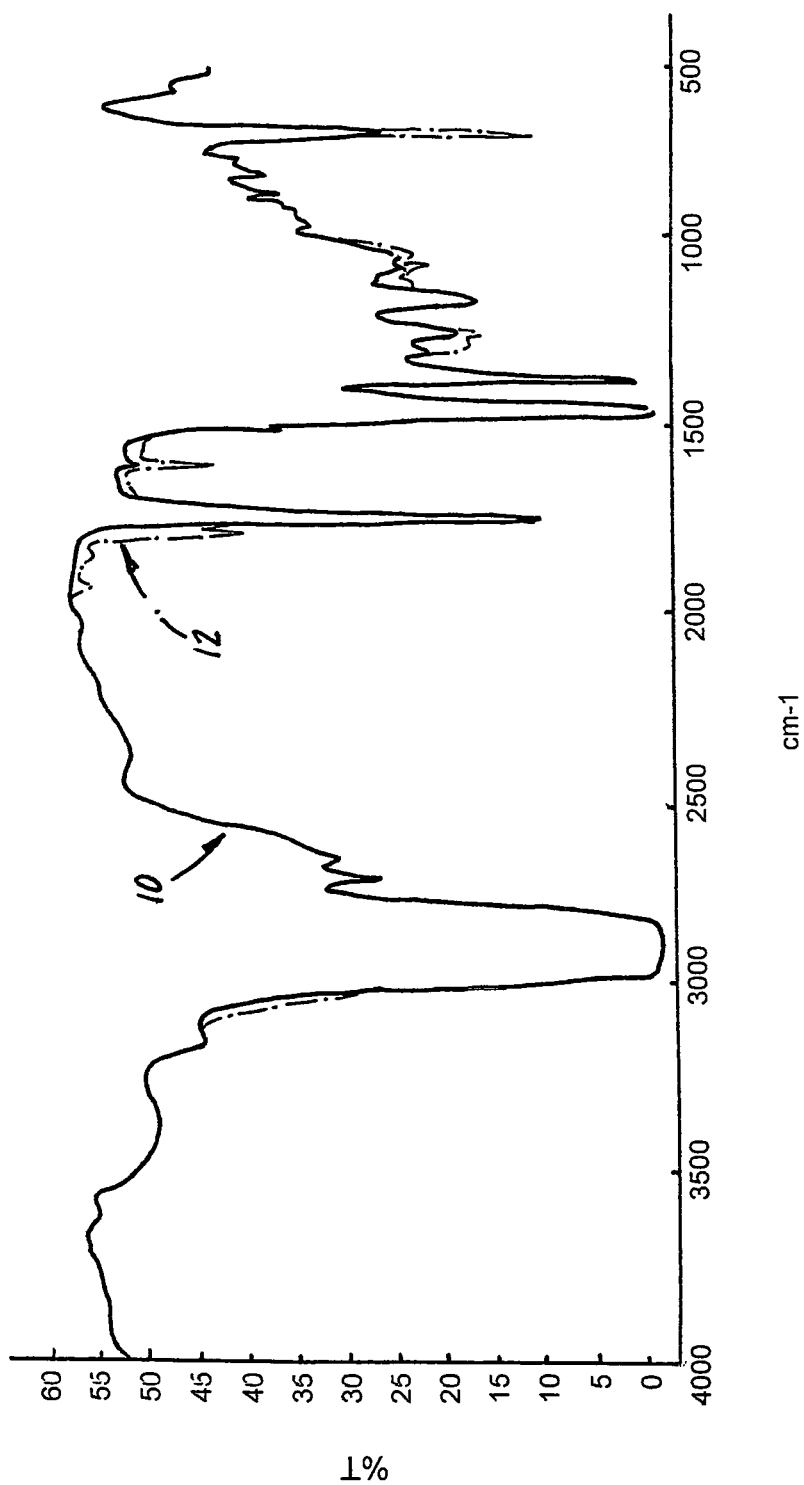

FIG. 5 is an overlay illustration of the FTIR scans for original lane oil (FIG. 1) and for the homogeneous fragrant combination (FIG. 4) of the original lane oil (FIG. 1) and the miscible fragrance composition (FIG. 2). FIG. 5 shows graph lines 10 (FIG. 1) and 12 (FIG. 4). In FIG. 5, graph line 12 is in dot-dash form and is largely coincident with and obscured by the solid graph line 10. The overlaid illustrations in FIG. 5 are nearly identical. In particular, the peaks at about 1700 $cm^{-1}$ (absorbance per centimeter) are very similar for the original lane oil (FIG. 1) and for the homogeneous fragrant lane oil (FIG. 4). The value in % T of the peak for the fragrant lane oil (FIG. 4) is within 10%, preferably 7.5%, more preferably 5%, and most preferably 4% of the % T for the peak for the original lane oil (FIG. 1). The close similarities of these peaks are desired in one embodiment of the invention and are believed to indicate that the fragrance composition of FIG. 2 does not adversely affect the properties of the lane oil of FIG. 1.

Fragrance compositions can, if desired, be admixed with lane conditioning oil prior to the lane conditioning oil being shipped from a remote location to a building structure. Such is not, however, presently preferred in the practice of the invention. One reason such is not presently preferred is that admixing a fragrance composition(s) with lane conditioning oil at the building structure avoids possible degradation or separation problems which may occur if a fragrance composition is admixed with lane oil at a location remote from the building structure. Another reason such is not presently preferred is that in some circumstances it may not be desirable to admix a fragrance composition every time lane oil is applied. Still another reason such is not preferred is that it provides a user located in the building structure with greater flexibility in selecting fragrance compositions with desired scents. Yet another reason such is not preferred is that it provides a user at the building structure with greater flexibility in the amount of a fragrance composition which is admixed with lane conditioning oil. A smaller building structure may only, for example, require one ounce of a fragrance composition in forty ounces of lane conditioning oil while a larger building structure may be better served by using two ounces of a fragrance composition in forty ounces of lane conditioning oil. Yet still another reason such is not preferred is that a user at the building structure may desire to add a fragrance composition to lane conditioning oil only after the lane conditioning oil is in the reservoir of the conditioning apparatus which is used to apply lane conditioning oil to a bowling lane.

Having described my invention in such terms as to permit those skilled in the art to make and use the invention, and having described presently preferred embodiments thereof, I claim:

1. A method to condition the air in a bowling alley comprising the steps of
   (a) providing an enclosed building structure;
   (b) providing a plurality of synthetic bowling lanes inside said structure, each of said lanes
      (i) including a first end with a base line,
      (ii) including a second end located under a pin setter, and
      (iii) extending from said first end to said second end;
   (c) providing a conditioning apparatus to apply lane oil separately to only a selected portion of each of said bowling lanes, said conditioning apparatus including
      (i) a reservoir to store a selected quantity of lane oil for dispensation on bowling lanes, and
      (ii) a oil dispensation mechanism to dispense oil at varying rates at different locations along a bowling lane while moving both
         toward said pin setter, and
         away from said pin setter;
   (d) shipping lane conditioning oil in at least one container from a remote location to said building structure, said lane conditioning oil comprising over 50% by weight mineral oil and having a medium to high viscosity in the range of 28.0 to 40.0 cSt at 40 degrees C. and having a surface tension in the range of 25 to 30 dynes/cm;
   (e) shipping a first fragrance composition in at least one container from a remote location to said building structure, said first fragrance composition having a scent and comprising a fragrance oil and carrier, said fragrance composition miscible in said lane conditioning oil in a proportion of fragrance composition to lane oil in the range of 1:80 to 1:10;

(f) shipping a second fragrance composition in at least one container from a remote location to said building structure, said second fragrance composition comprising a fragrance oil and carrier, said fragrance composition miscible in said lane conditioning oil in a proportion of fragrance composition to lane oil in the range of 1:80 to 1:10, said second fragrance composition having a scent different from the scent of said first fragrance composition;

(g) homogeneously admixing said first fragrance composition and said lane conditioning oil at said building structure in a proportion in the range of 1:80 to 1:10 to produce a first fragrant lane oil having in an FTIR a % transmittance (% T) at 1700 $cm^{-1}$ that is within 5% or less of the % T of said lane conditioning oil at 1700 $cm^{-1}$;

(h) utilizing said conditioning apparatus to apply said first fragrant lane oil to one of said synthetic lanes while said conditioning apparatus is both moving away from and moving toward said base line such that (i) the thickness of said first fragrant lane oil on said lane adjacent said base line is at least thirty units, (ii) the thickness of said first fragrant lane oil a first selected distance away from said base line is greater than zero, but less than fifteen units, and (iii) there is no first fragrant lane oil a second selected distance away from said base line, said second selected distance being greater than said first selected distance;

(i) repeating, after a selected period of time has passed, steps (g) and (h) except that said second fragrance composition is substituted for said first fragrance composition.

* * * * *